(12) United States Patent
Buck et al.

(10) Patent No.: US 6,254,566 B1
(45) Date of Patent: *Jul. 3, 2001

(54) TAMPON WITH A TAMPON APPLICATOR

(75) Inventors: Kimberly Ann Buck; Lisa Ann MacKay, both of Cincinnati, OH (US); William Patton Peace, Lawrenceburg, IN (US); Chrissie Melinda Smits; Richard Tweddell, III, both of Cincinnati, OH (US); Eric Patton Weinberger, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/336,468

(22) Filed: Jun. 18, 1999

(51) Int. Cl.[7] ............................................ A61F 13/20
(52) U.S. Cl. .............................................. 604/15; 604/904
(58) Field of Search ............................. 604/904, 11–18, 604/285, 286, 57, 59, 60, 311

(56) References Cited

U.S. PATENT DOCUMENTS

| | | | |
|---|---|---|---|
| 1,969,671 | * 8/1934 | Nelson | 604/15 |
| 3,762,413 | * 10/1973 | Hanke | 604/14 |
| 4,592,740 | * 6/1986 | Mahruki | 604/15 |
| 5,080,659 | * 1/1992 | Nakanishi | 604/904 |
| 5,554,108 | * 9/1996 | Browning et al. | 604/15 |
| 5,873,971 | * 2/1999 | Balzar | 604/904 |

* cited by examiner

*Primary Examiner*—Dennis Ruhl
(74) *Attorney, Agent, or Firm*—Theodore P. Cummings; Matthew P. Fitzpatrick; Kevin C. Johnson

(57) ABSTRACT

A suitable tampon with a tampon applicator for expelling the tampon to provide side-to-side coverage and inserting the tampon into a body cavity is provided. The tampon applicator has a tampon holder tube having interior and exterior surfaces, a longitudinal axis, a hollow portion and an expulsion end dimensioned for insertion into the body cavity. The tampon holder tube has a feature for separating and spreading a tampon apart during expulsion of the tampon. A plunger may also be telescopically and slidably mounted in the tampon holder tube distal to the expulsion end and adapted to directionally expel the tampon from the tampon holder tube when a user expels the tampon from the tampon holder tube.

17 Claims, 10 Drawing Sheets

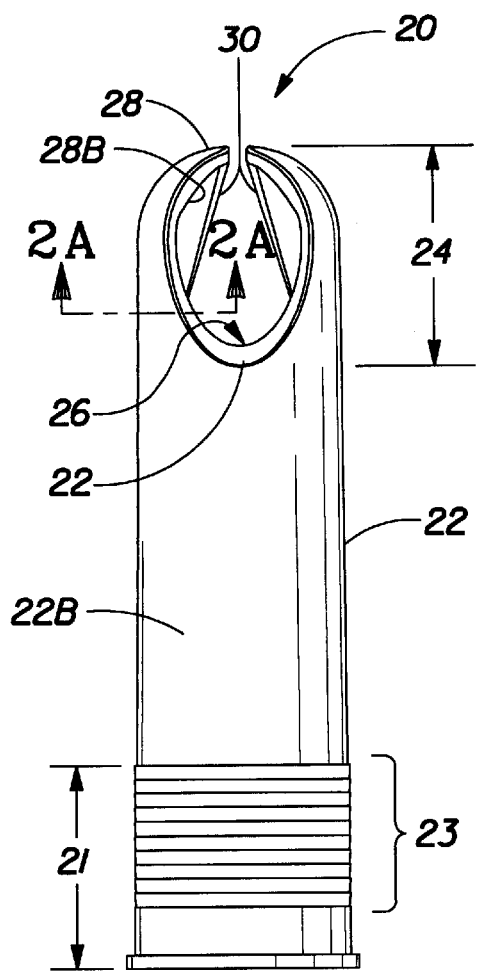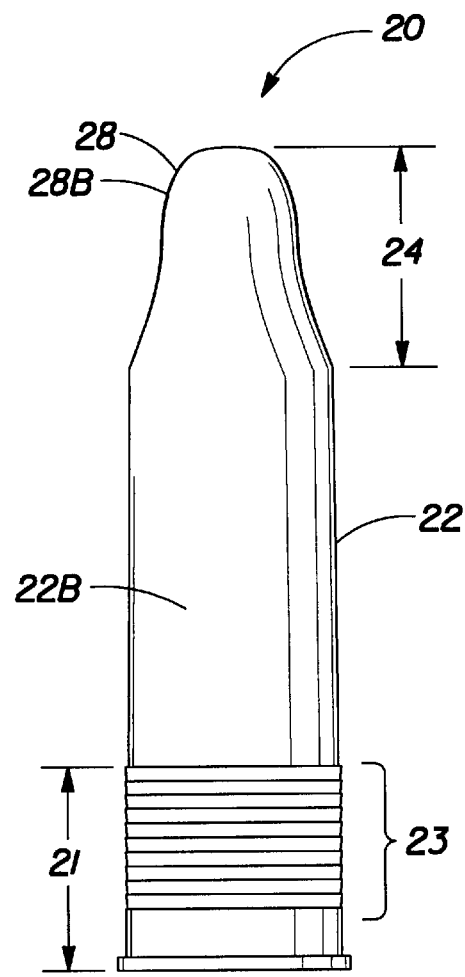
FIG. 2    FIG. 3
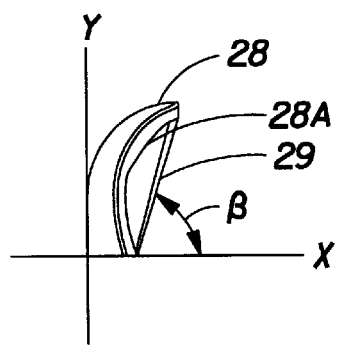
FIG. 2A

TAMPON WITH A TAMPON APPLICATOR

FIELD OF THE INVENTION

The invention provides a novel tampon applicator having a tampon expulsion feature providing directed expulsion of a tampon.

BACKGROUND OF THE INVENTION

Tampon applicators comprising a plurality of telescopically-arranged tubes are known. Such applicators are, however, either blunt ended at the end which is intended for vaginal insertion (the "expulsion end ") or, in recent years applicators have been developed which are rounded at that end, having a plurality of separated "petals" which are further spaced upon the expulsion through the end of a tampon. The telescopic tube arrangement permits one tube to be used as a plunger to force the expulsion of the tampon from another tube in which the plunger tube is slidably positioned. Although the petal format is more convenient for vaginal insertion, the prior art structures suffer from a number of disadvantages, the most significant of which is probably the tendency of the expanded petal arrangement (after expulsion of a tampon) to catch or nip tissue and hair. By way of example, a petal-type tampon applicator made from plastics material is known in which the rounded tampon expulsion end comprises a number of separated petals integrally formed with the remainder of the upper part of the tampon applicator. The petals each come to a point so that the rounded end, before expulsion of a tampon, is closed and has the appearance in end-on view of a circle split into a number of segments. Unfortunately, the petals of this structure have a tendency to nip or catch tissue or hair therebetween when the applicator is in use this tendency is exacerbated by the petals readily springing back to the original configuration after expulsion of a tampon. Existing long petal arrangements also exhibit a problem which arises from the less stable expulsion end configuration produced by long petals. The resulting less stable formed end may produce user discomfort because of the increased risk of the petals being bent back during vaginal insertion.

Additionally, it has been long recognized that the internal vaginal cavity in its normal collapsed state is of much wider dimension in its transverse plane than in its vertical plane. It is equally well known that the minimum dimension of the vagina is near the introitus while the maximum dimension is near the cervix. It is desirable, therefore, when considering a tampon for catamenial use, to provide a structure which is in its initial state is of a size small enough to pass through the vaginal orifice without discomfort, and when once inside the vaginal cavity and beyond the restrictions of the orifice may be expanded, particularly in the lateral direction, to contact substantially large portions of the vaginal walls, preferably from one side to the other in the vaginal cavity to prevent early bypass of the menstrual discharges from the cervix. Note that this side-to-side coverage is a highly preferred object of this invention. Since the vaginal wall in its normal collapsed state is flaccid and has multiple folds and wrinkles which provide channels through which a significant portion of the menstrual fluids normally flow, it is also important that the absorbent tampon be as soft and conformable as possible in order to conform to the shape of the vaginal cavity and fit within these channels to minimize leakage.

The absorbent catamenial tampons now in general use comprise small, highly compressed, cylindrical plugs about three-eighths to one-half inch (about 1.0 cm to 1.3 cm) in diameter and from 1 ½ to 2 ½ inches in length (about 3.8 cm to 6.4 cm). Because of the need for absorbent capacity, they are usually formed from batts much larger in size than the vaginal orifice, and compressed to the small size indicated above in order to facilitate insertion. As fluid is absorbed, these compressed tampons are expected to re-expand toward their original pre-compressed size, and to eventually become large enough to effectively cover the vaginal cavity against fluid leakage or bypass. While it has been found that these compressed tampons perform their intended function tolerably well, even the best of them do not re-expand sufficiently, or fast enough, to provide good transverse coverage against leakage even though the vertical block may be satisfactory. Further, most of these tampons often use only a small portion of their absorptive capacity before leakage. Since these tampons rely on some fluid absorption to re-expand, it is clear that fluid bypass and leakage can occur prematurely, and can particularly occur immediately or soon after the time of insertion.

Numerous attempts have been made to solve this problem with some approaches focusing on the applicator and others focusing on the tampon itself For example, some approaches in the patent art suggest a tampon with a built-in mechanical expansion means, a typical example being U.S. Pat. No. 3,706,311 to Kohx, et al. However, the mechanical expansion means disclosed in that patent is in the form of a flat spring-like element which after insertion permanently maintains the spread configuration of the tampon, may make it difficult to remove.

Another approach is described in U.S. Pat. No. 3,512,528 to Whitehead, et al. which teaches the use of a sack of absorbent material collapsed to a small size for insertion and which after insertion is expanded by the introduction of a gas or a fluid internally of the sack. The multiple steps and complicated manipulation of the gas or fluid introduction means required when using this type of tampon detract from the tampon.

Still another approach is described in U.S. Pat. No. 3,857,395 issued to Johnson, et al. The Johnson, et al. patent teaches the use of an elongated inserter device over which a flat tampon is draped. The inserter is said to permit the draped portion of the tampon to be pulled, rather than pushed into the cavity from the point at which the tampon is supported on the leading end of the inserter. The inserter means is equipped with a bilateral expansion mechanism which at the user's option may be operated to transversely spread the tampon at the time of insertion. The inserter device described in the Johnson, et al. patent suffers from many drawbacks, however. The Johnson inserter device is a complicated device comprising a pair of hinged arms that are capable of laterally diverging at a hinge or joint. The angular nature of the hinged arms would make that inserter uncomfortable to use. The complex nature of the hinged arms would also make it difficult and expensive to manufacture. As a result, it would not be suitable as a disposable applicator.

Another problem that exists in deploying tampons having a greater transverse dimension within the vaginal cavity is that this greater transverse dimension of the vaginal cavity is roughly perpendicular to the vaginal opening.

One attempt to address this latter problem is described in U.S. Pat. No. 3,068,867 issued to Bletzinger, et al. The Bletzinger, et al. patent is directed to a tampon insertion device having a positioning indicator thereon. The device described in the Bletzinger, et al. patent comprises an insertion device for tampons which are either of cylindrical cross-section, or non-cylindrical cross-section but constructed to exp and w hen subjected to fluids in a non-cylindrical shape. The insertion device is provided with an indicator that aids the user in inserting the tampon with its major cross-sectional axis transverse to the major axis of the vaginal opening. The Bletzinger device, however, is awkward in that it requires insertion of the widest dimension of the tampon cross-wise to the narrowest dimension of the vaginal opening.

Another series of attempts to overcome the problems associated with conventional, highly compressed, fluid expanding tampons is described in U.S. Patent No. 3,749,094 issued to Duncan and U.S. Patent Nos. 3,794,029 and 3,766,921 both issued to Dulle. The Duncan and Dulle devices are all generally conical and are designed to be dry-expanding. While these devices would be expected to overcome some of the problems associated with highly compressed, fluid expanding tampons, the Duncan and Dulle devices still require significant rigidity and compression in order to permit their use in a conventional "tube and plunger" type applicator for which they are designed. It has been found during development of the present invention that a tampon constructed according to the invention described herein can provide even further improvements in comfort, low wearing awareness, and performance as compared to currently marketed tampons and previous attempts to improve upon such tampons such as those described above. The present invention aims to provide a structure with the advantages of petal-type applicators, and especially providing for side-to-side coverage, but minimizing the disadvantages noted above.

SUMMARY OF THE INVENTION

Accordingly, the invention provides a suitable tampon with a tampon applicator for directionally inserting the tampon into a female's vaginal cavity.

More specifically, a tampon and a tampon applicator are provided in combination for directional expulsion of the tampon into the vaginal cavity of a female user. The tampon applicator provides a tampon holder tube having a hollow portion, interior and exterior surfaces, a longitudinal axis, an expulsion end dimensioned for insertion into the body cavity, and an insertion end positioned oppositely to the expulsion end. The tampon holder tube comprises a feature for directionally expelling a tampon into the vaginal cavity of a female user. In practice, a tampon is loaded into the tampon holder tube in a pre-expelled position, and a plunger telescopically and slidably mounted in the tampon holder tube at the insertion end of the tampon holder tube, the plunger being adapted to expel the tampon from the tampon holder tube.

In one embodiment herein, the feature that directionally expels a tampon will partially separate at least one portion of the tampon into at least two distinct portions as the tampon is directionally expelled from the tampon holder tube. In another embodiment herein, the feature for directionally expelling a tampon substantially separates at least one portion of the tampon into at least two distinct portions as the tampon is expelled from the tampon holder tube.

In one preferred embodiment herein, the tampon may comprise one longitudinal portion having two opposed ends and a mid-section; the tampon is preferably uninterrupted by any breaks therein. Such a tampon is loaded into the tampon holder tube by bending the tampon at about the tampon's middle portion or mid-section and positioning the tampon's opposed ends into adjacent proximity to one-another.

In another tampon embodiment herein, the tampon comprises one longitudinal portion having two opposed ends and a mid-section, the tampon being interrupted at the mid-section to form a shape. Such an interrupted tampon consists of one or more of the following shapes: cylinders, circles, V-shapes, U-shapes, crimped shapes, hexagons, triangles, orthogonals, pentagons, squares and combinations thereof As mentioned above, the tampon holder tube comprises a feature for directionally expelling a tampon. The feature comprises a pair of mutually opposed guides extending from the expulsion end. Each guide preferably has a continuous external surface and an internal surface opposed thereto wherein the continuous external surface faces away from the hollow of the tampon holder tube and the opposing internal surface faces inwardly toward the hollow of the tampon holder tube. In this embodiment, the internal surfaces each have a guidance plate positioned inwardly toward the hollow of the tampon holder tube. Each guidance plate further comprises at least one pair of guidance ridges that have a continuous surface positioned therebetween; i.e., more than one pair of guidance ridges may reside on each internal surface of each guide. Further, the guides preferably have a pair of sloping surfaces, each sloping surface being positioned connectedly adjacent to a guidance ridge and each sloping surface sloping from the guidance ridge to the internal surface of the guide adjacent to the free expulsion area. The tampon applicator further preferably comprises a pair of free expulsion areas positioned adjacent to the guides. The free expulsion areas and the guides operate together to provide efficient directional expulsion of a tampon. Preferably, a plunger is telescopically and slidably mounted in the tampon holder tube distal to the expulsion end and adapted to expel a tampon from the tampon holder tube when a user expels the tampon.

In another embodiment herein, a tampon applicator for directionally expelling a tampon is provided. This tampon applicator comprises a tampon holder tube having a hollow, interior and exterior surfaces, a longitudinal axis, and an expulsion end dimensioned for insertion into the female's vaginal cavity. The tampon holder tube comprises a feature for directionally expelling a tampon. The feature comprises a pair of opposed guides extending from the expulsion end, each said guide having a discontinuous external surface and an internal surface opposed thereto. The discontinuous external surface faces away from the hollow of the tampon holder tube and the opposing internal surface faces toward the hollow of the tampon holder tube. The discontinuous external surfaces are preferably indented inwardly toward the hollow of the tampon applicator. Each indentation operates to form an indented guidance plate on the internal surface of each guide. The feature preferably further comprises a pair of opposed free expulsion areas, the free expulsion areas being positioned adjacent to the guides on the tampon holder tube. The free expulsion areas and the guides operate together to provide efficient directional expulsion of a tampon. Preferably, a plunger is telescopically and slidably mounted in the tampon holder tube distal to the expulsion end and adapted to expel a tampon from the tampon holder tube when a user expels the tampon.

In yet another embodiment herein, a tampon applicator for directionally expelling a tampon is provided that comprises a tampon holder tube having a hollow, interior and exterior surfaces, a longitudinal axis, and an expulsion end dimensioned for insertion into the female's vaginal cavity. The tampon holder tube comprises a feature for directionally expelling a tampon. The feature further comprises at least a pair of opposed guides extending from the expulsion end.

Each guide has an external surface and an internal surface opposed thereto, wherein the external surface faces away from the hollow of the tampon holder tube and the opposing internal surface faces inwardly toward the hollow of the tampon holder tube. The internal surfaces each comprise a guidance plate having at least one pair of guidance ridges, i.e., more than one pair of guidance ridges may reside on each internal surface of each guide. The guidance plates herein do not provide a continuous surface between the guidance ridge pairs. Each guidance ridge preferably, but not necessarily, substantially extends throughout the expulsion end of the tampon holder tube and may each be comprise a sloping surface positioned adjacent to each guidance ridge. The feature preferably further comprises a pair of opposed free expulsion areas. The free expulsion areas are positioned adjacent to the guides on the tampon holder tube. The free expulsion areas and the guides operate together to provide directed expulsion of a tampon. Preferably, a plunger is telescopically and slidably mounted in the tampon holder tube distal to the expulsion end and adapted to expel a tampon from the tampon holder tube when a user expels a tampon.

For each of the tampon applicator embodiments noted above, the guidance plates therein may be inwardly oriented towards the hollow of the tampon holder tube at an angle $\beta$ ranging from about 0° to about 89°. Preferably, each guidance plate herein is inwardly oriented towards the hollow of the tampon holder tube at an angle $\beta$ ranging from about 10° to about 80°. More preferably, each guidance plate is inwardly oriented towards the hollow of the tampon holder tube at an angle R ranging from about 20° to about 70°.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

FIG. 2 is a plan side view of the tampon applicator of FIG. 1;

FIG. 2A is a side cut view of the left oriented guide and guidance plate of FIG. 2;

FIG. 3 is plan side view of the embodiment of FIG. 2 turned 90° to the right;

DETAILED DESCRIPTION OF THE INVENTION

Figure 14A:
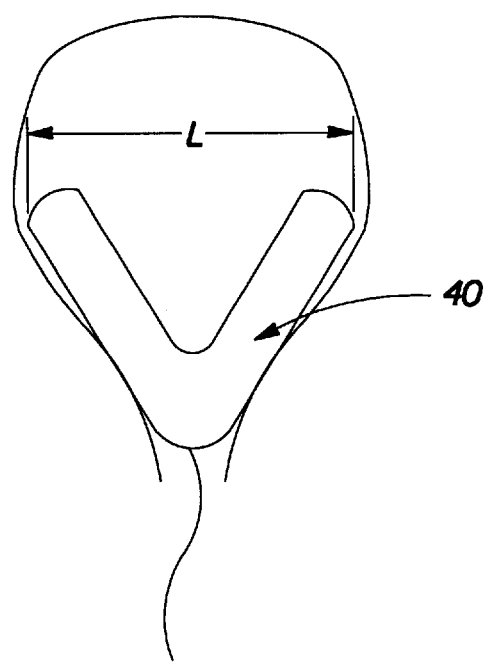
FIG. 14A is a plan view of a tampon embodiment of the present invention fitting within the vaginal cavity of a female user.
Figure 14B:
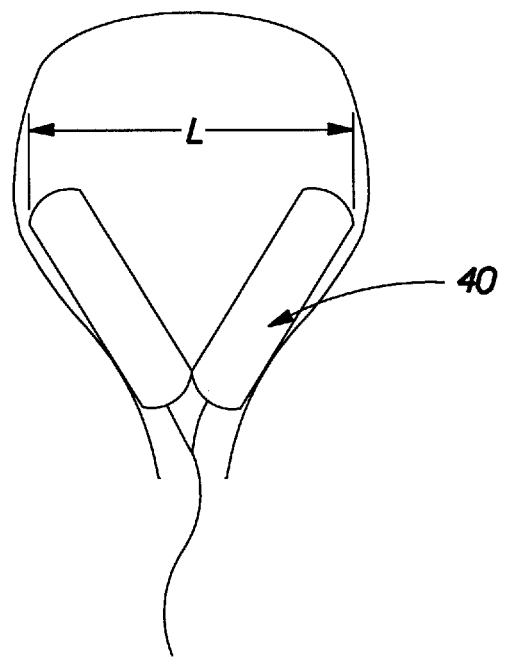
FIG. 14B is a plan view of an alternative tampon embodiment of the present invention fitting with the vaginal cavity of a female user.

By the terms "directionally expel", "directed expulsion" or "directional expulsion" it is meant herein that embodiments of the tampon applicators of the present invention will either 1) cause a suitable tampon herein to substantially divide into at least two portions and expel angularly (i.e., at an angle) as the tampon is expelled through the tampon applicator; and/or 2) directionally position a tampon to be placed adjacent to the walls of a female user's vaginal cavity. By the term "angularly" it is meant herein that a tampon herein at expulsion from a tampon holder tube will expel at an angle divergent from the longitudinal axis of the tampon applicator. Such directional expulsion causes the tampon applicator, when inserted into the vaginal cavity of a female user, to spread the tampon in the transverse direction thus providing side to side coverage to the sides of a female user's vaginal cavity. By the term "side-to-side coverage" it is meant herein that the tampon, once directionally expelled, will have at least two sections thereof positioned outwardly onto the sides or walls of a female user's vaginal cavity (See FIGS. 14A and 14B).

Figure 1:
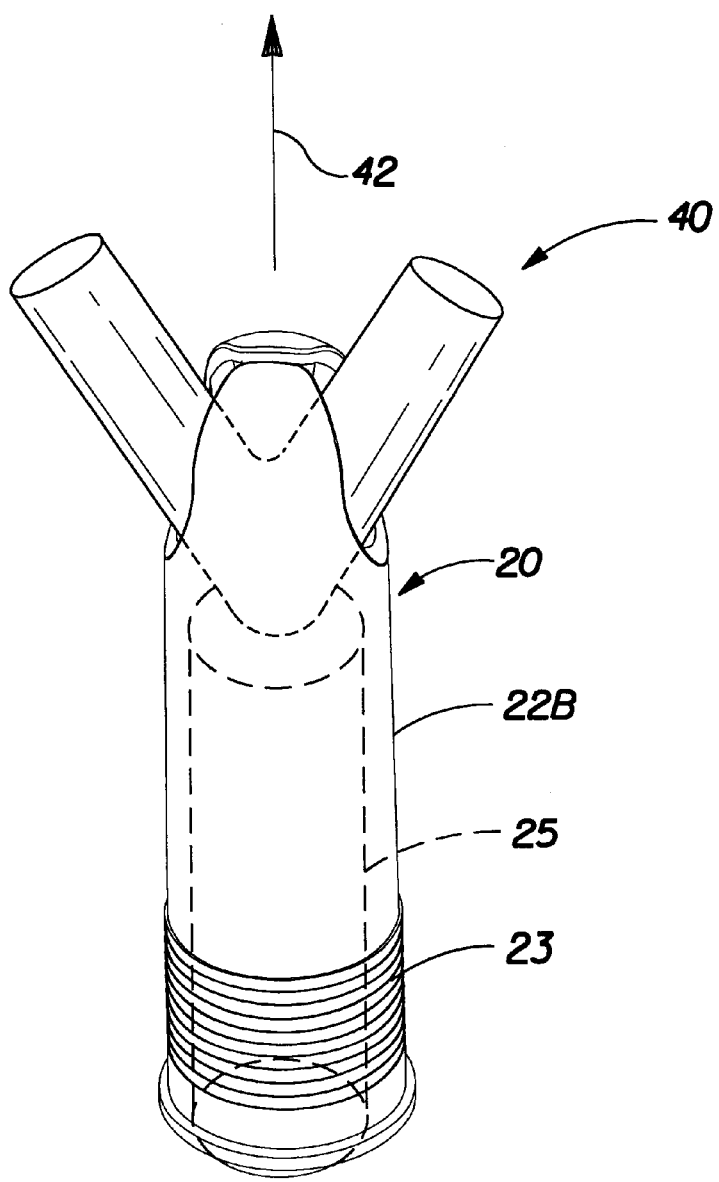
FIG. 1 is a perspective drawing of a tampon applicator and tampon being expelled therethrough.
Figure 4:
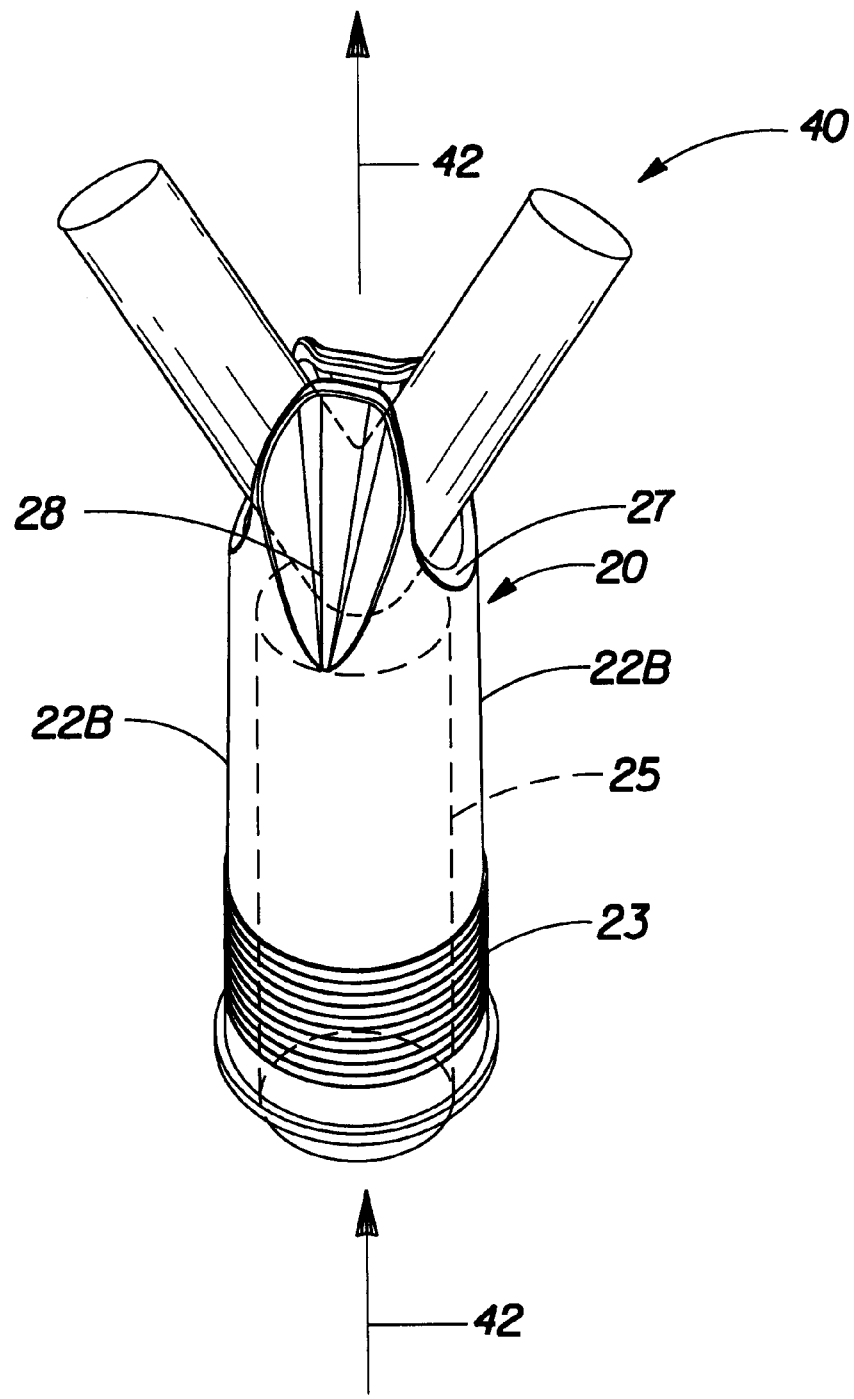
FIG. 4 is a perspective view of an alternative embodiment of a tampon applicator herein.

A tampon and a tampon applicator are provided in combination for directional expulsion of the tampon into the vaginal cavity of a female user (FIG. 1). The tampon applicator 20 provides a tampon holder tube 22 having a hollow portion 26' (not shown), interior 28A and exterior surfaces 28B (FIG. 2), a longitudinal axis 42, an expulsion end 24 dimensioned for insertion into the body cavity, and an insertion end 21 positioned oppositely to the expulsion end 24. The tampon holder tube 22 comprises a feature for directionally expelling a tampon 40 into the vaginal cavity of a female user. In practice, a tampon 40 is loaded into the tampon holder tube 22 in a pre-expelled position, and a plunger 25 telescopically and slidably mounted in the tampon holder tube 22 at the insertion end 21 of the tampon holder tube, the plunger being adapted to expel the tampon from the tampon holder tube.

In one embodiment herein, the feature that directionally expels a tampon will partially separate at least one portion of the tampon into at least two distinct portions as the tampon is directionally expelled from the tampon holder tube. By the term "partially separate" it is meant herein that as a tampon 40 is expelled through the tampon holder tube 22, at least two portions, but not necessarily the entire tampon, will partially, but not fully or substantially, separate apart from one-another (See FIG. 11). In another embodiment herein, the feature for directionally expelling a tampon substantially separates at least one portion of the tampon into at least two distinct portions as the tampon is expelled from the tampon holder tube. By the term "substantially separate" it is meant herein that as a tampon 40 is expelled through the tampon holder tube 22, at least two portions, but not necessarily the entire tampon, will substantially separate apart from one-another (See FIGS. 1, 9, and 12B).

Figure 12A:
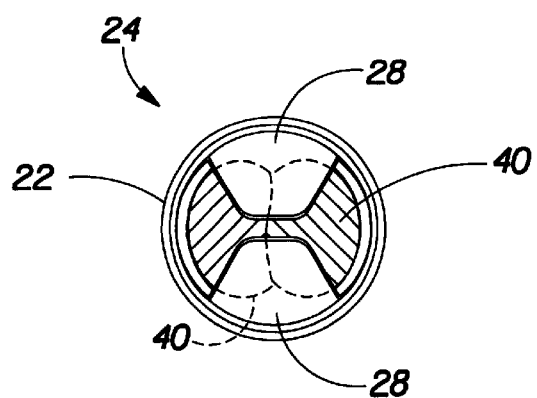
FIG. 12A is a top view of a tampon in its pre-expelled position in a tampon applicator.

In one preferred embodiment herein, the tampon 40 may comprise one longitudinal portion (FIG. 14A) having two opposed ends and a mid-section; the tampon is preferably uninterrupted by any breaks therein. Such a tampon 40 is loaded into the tampon holder tube 22 by bending the tampon 40 at about the tampon's middle portion or mid-section and positioning the tampon's opposed ends into adjacent proximity to one-another (FIG. 12A). By the term "adjacent proximity" it is meant herein that the two ends of the tampon 40 when loaded into a tampon holder tube 22, as shown in FIG. 12A, will be positioned close together in the tube 22 prior to expulsion of the tampon 40.

Figure 11:
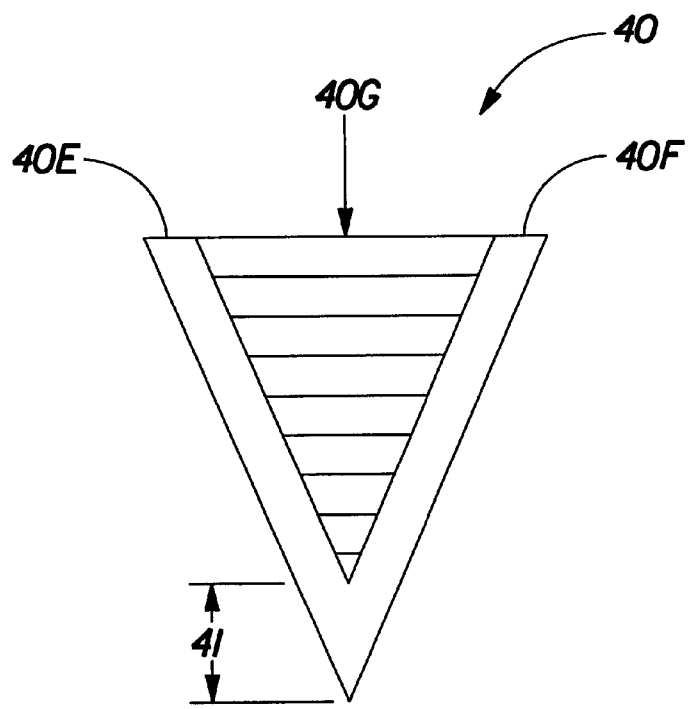
FIG. 11 is a plan view of a substantially solid tampon.
Figure 12B:
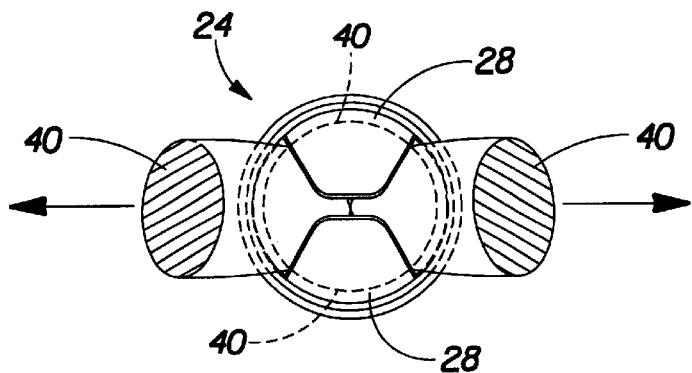
FIG. 12B is a top view of a tampon during its expulsion from the tampon applicator.
Figure 13:
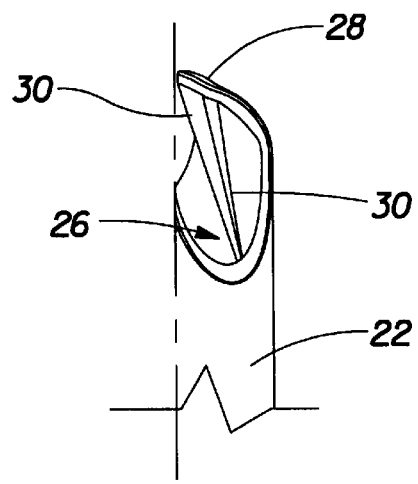
FIG. 13 is a partial perspective view of a guide at the expulsion end of the tampon applicator.

In another tampon embodiment herein shown in FIG. 11, the tampon 40 comprises one longitudinal portion having two opposed ends 40E and 40F and a mid-section 41, the tampon 40 being interrupted at the mid-section 41 to form a shape. By the term "interrupted" it is meant herein that the tampon 40 is bent and/or shaped permanently so as not to conform to a cylindrical or straightened shape. Such an interrupted tampon 40 consists of one or more of the following shapes: circles, V-shapes, U-shapes, crimped shapes, hexagons, triangles, orthogonals, pentagons, squares and combinations thereof. As is shown in FIG. 1, the present invention provides a directionally expelling tampon 40 in combination with a tampon applicator 20 for directional expulsion of the tampon 40. The tampon applicator 20 herein comprises a tampon holder tube 22 having an interior surface 22A (not shown), an exterior surface 22B (FIGS. 1–3), a longitudinal axis 42 (FIG. 1), a hollow portion 26' (not shown) surrounded by the tampon holder tube 22 and an expulsion end 24 (FIGS. 2–3) dimensioned for insertion into the body cavity, specifically the vaginal cavity of a female user. The hollow portion 26' represents the open space which is surrounded by the tampon holder tube 22. Additionally, the tampon holder tube 22 further comprises a feature for directionally expelling a tampon 40 during its expulsion through the tampon holder tube 22. Alternatively, the tampon applicator 20 may include a plunger 25 (FIG. 1) that is telescopically and slidably mounted in the tampon holder tube 22 distal to the expulsion end 24 and adapted to expel the tampon 40 from the tampon holder tube 22 when a female user expels the tampon 40 from the tampon holder tube 22. However, such user activated expulsion may occur either by a plunger 25, plunger-like device or digitally with a user's finger(s), FIG. 1 further shows a tampon 40 partially positioned within and without of the tampon holder tube 22 of the tampon applicator 20 in the act of expulsion of the tampon 40. Previous to expulsion, the tampon 40 rests in a ready or pre-expelled position in the tampon holder tube 22 poised for expulsion (FIG. 12A). By the terms "ready position" or "pre-expelled position" it is meant herein a position in which the tampon 40 is placed or packed into the tampon holder tube 22 positioned for the tampon's successful expulsion through the tampon holder tube 22. As is readily seen in FIG. 12A, the tampon 40 preferably sits within the tampon holder tube 22 and can remain preferably snugly therein without any outside force to sustain its position in the tampon holder tube 22. In FIG. 12B, i.e., during the expulsion of the tampon 40, the tampon 40 is shown being directionally expelled such that when the tampon applicator 20 is inserted into the vaginal cavity of a female user, side-to-side coverage is achieved. Note that a tampon applicator 20 herein is inserted into the vagina of a female user while the tampon 40 sits therein in its pre-expelled position.

Figure 15:
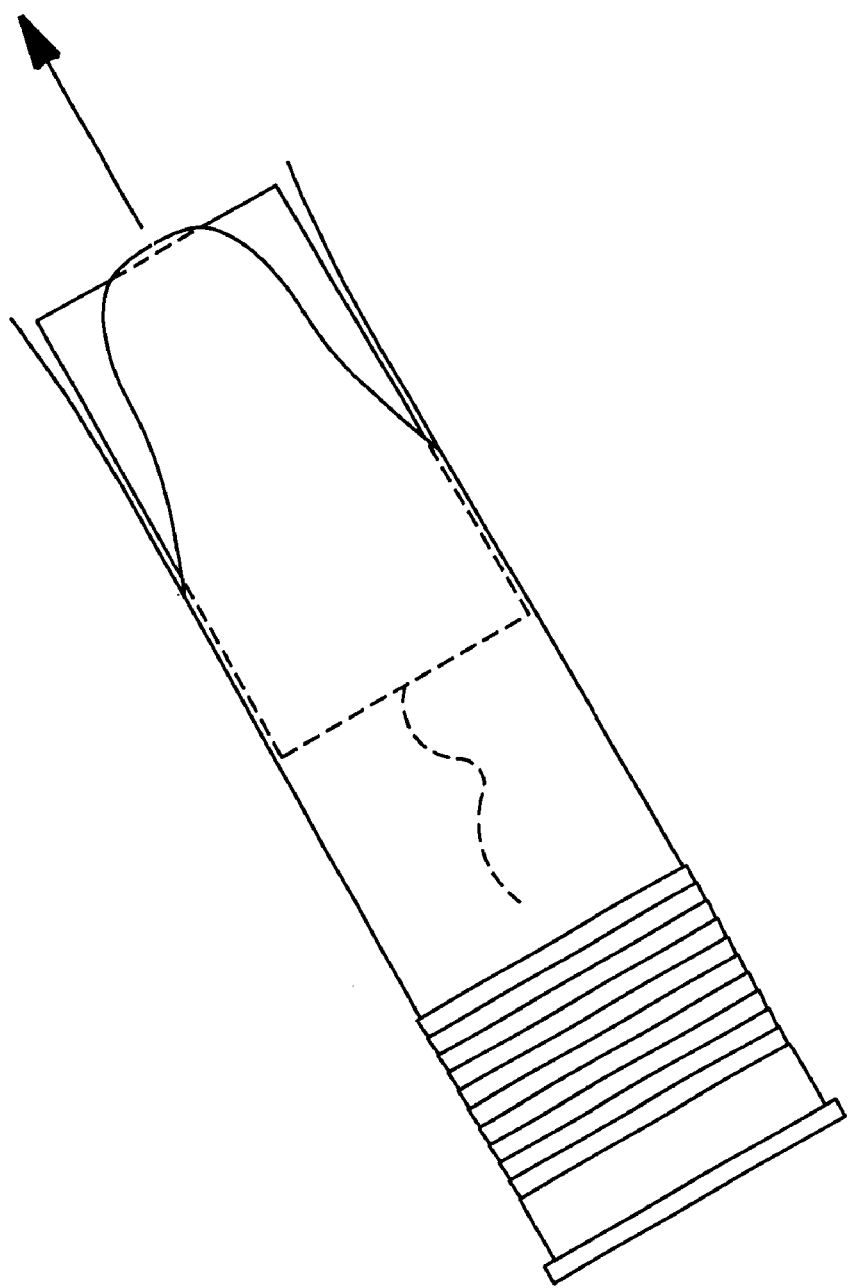
FIG. 15 is a schematic side view of a typical PRIOR ART device.

The purpose of directional expulsion is to achieve side-to-side coverage of a tampon 40 within a female user's vaginal cavity. While not wishing to be bound by any particular theory, it is believed herein that side-to-side coverage is best achieved when the tampon 40, during expulsion, is directed by the unique design of the tampon applicators shown in the figures; not including, of course, the prior art device (FIG. 15).

Figure 9:
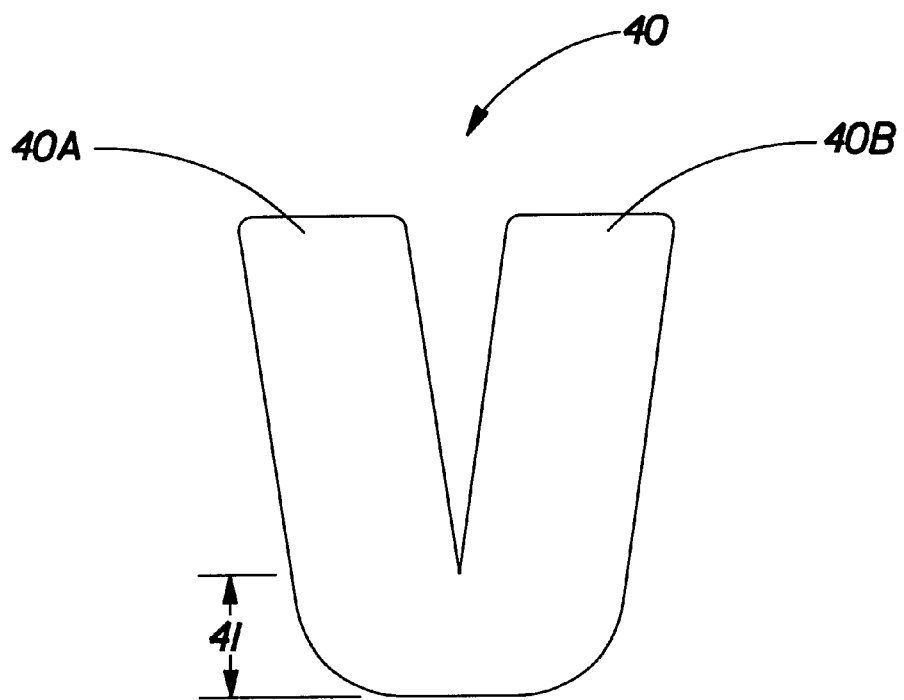
FIG. 9 is a plan view of a tampon having un-joined sections.
Figure 10:
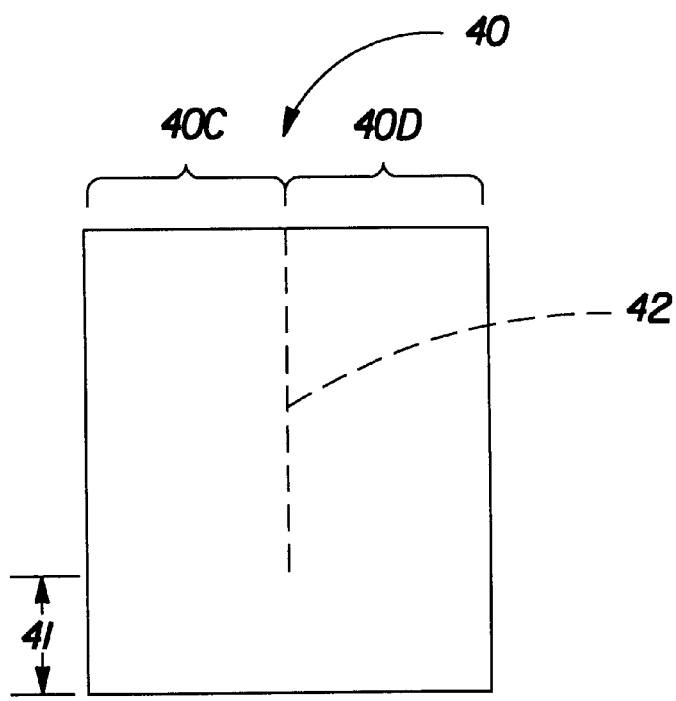
FIG. 10 is a plan view of a tampon having semi-joined sections.

The tampon 40 itself may comprise, i.e., come in, several forms. For example, the tampon 40 may comprise at least two longitudinally unjoined sections 40A and 40B and a base or joining section 41. (FIG. 9). By the term "unjoined" it is meant herein that a portion of the tampon will have two or more portions which are not substantially connected to one-another. In another form of the tampon 40 herein, the tampon 40 may comprise at least two longitudinally semi-joined sections 40C and 40D. (FIG. 10). By the term "semi-joined" it is meant herein that two or more portions of the tampon are joined about one more lines of weakness 42 (FIG. 10) upon which the force of expulsion of a tampon may disrupt. By the term "line(s) of weakness" it is meant herein a line or area capable of being disrupted thereby causing a tampon to split into two or more portions as it is expelled through the tampon applicator. One example of a line of weakness 42 is a line of perforation 42, the line of perforation residing between at least two semi-joined portions 40C and 40D. (FIG. 10).

In another embodiment herein, the tampon 40 may be a substantially solid device. (FIG. 11). By the term "substantially solid" it is meant herein that the tampon comprises portions of substantially solid density, and the tampon is not readily susceptible to being divided into two or more portions by the guidance ridges of the tampon applicator. As one example herein of a substantially solid tampon, the tampon 40 may comprise sections of varying density positioned longitudinally about the longitudinal axis 42 of the tampon applicator 20. More specifically, the sections of the tampon 40 may comprise semi-compressed or compressed material throughout the tampon sections. Preferably, as in FIG. 11 tampon, this substantially solid device comprises two acquisition portions 40E and 40F with an absorbent portion 40G positioned therebetween. Preferably, a base or joining section 41 is positioned at one end of the tampon 40.

Contact of a female user's vaginal walls is a highly desired characteristic of a tampon when it is worn during a female's menstruation period. Menses, whether highly viscous or less viscous, when leaching out of user, follows the geometry of a female user's vaginal walls. In other words, menses may substantially flow along the vaginal walls of a female user. For example, FIGS. 14A and 14B, which show two different embodiments of tampons 40 providing side-to-side coverage, show how such side-to-side coverage is expected to occur. More specifically, whether a tampon 40 comprises one section or is multi-sectional by use of the tampon applicator 20 which provides directional expulsion of a tampon 40, side-to-side coverage of the tampons 40 to a female's vaginal sides is expected to occur the same as or similar to that side-to-side coverage shown in FIGS. 14A and 14B.

Figure 5:
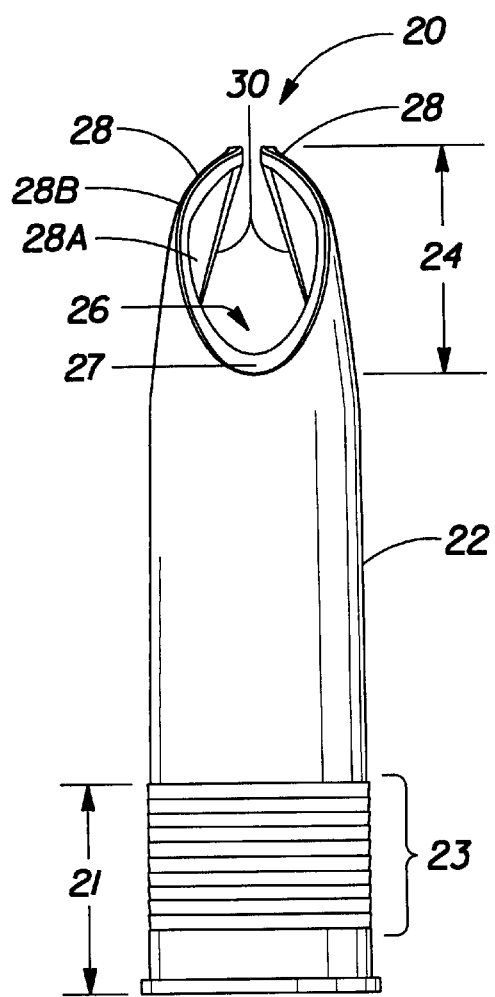
FIG. 5 is a plan side view of the tampon applicator of FIG. 4.
Figure 6:
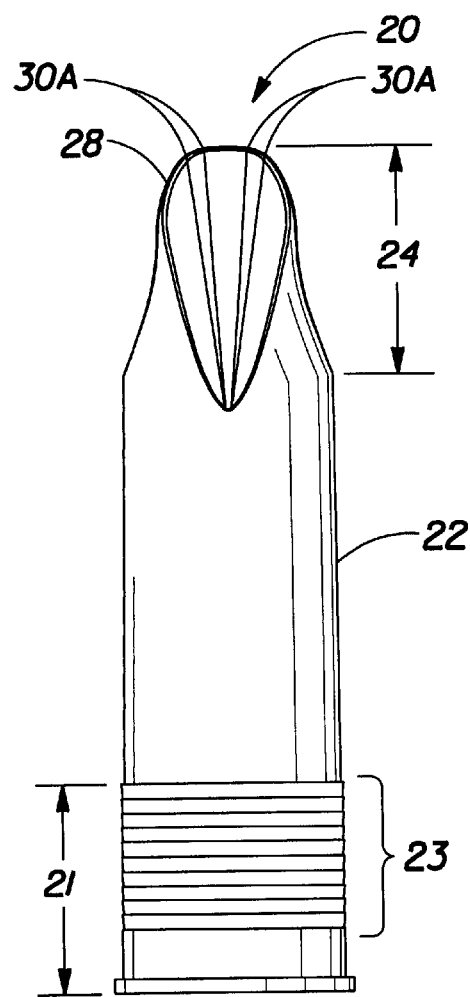
FIG. 6 is a plan side view of the tampon applicator of FIG. 5 turned 900 to the right.

FIGS. 1–3 show that the feature for directionally expelling the tampon 40 apart during the expulsion thereof comprises at least one pair of guides 28. The guides 28 each have an external surface 28B and an internal surface 28A (FIG. 5). The guides 28 are positioned at the expulsion end 24 of the tampon applicator 20 and have a pre-expelled position. By the term "pre-expelled position" it is meant herein that position occupied by the guides 28 before they are impacted or contacted by a suitable tampon 40 expelled from the tampon applicator 20; e.g., see FIG. 2 as an example of guides 28 in their pre-expelled positions. The guides 28 operate to remain substantially close to their pre-expelled position during the expulsion of part of the tampon 40 from the tampon holder tube 22. In an alternative embodiment herein, the guides 28 may actually touch or be connected at their respective tips such one guide 28 results. Herein, the guides 28 are made more rigid than guides or petals on conventional applicators because of their designed task; i.e., directional expulsion of a tampon. Guide rigidity and their effects on suitable tampons will be discussed in greater detail hereafter.

On the internal surfaces 28A of each guide 28 are located guidance plates 29 (FIG. 2A). Each guidance plate 29 operates in conjunction with the guides 28 to help directionally expel a tampon 40 from the tampon holder tube 22. More specifically, the guidance plates 29 provide angled surfaces that operate to expel a tampon 40 from the tampon holder tube 22 at an angle, such angularity being provided by the design of a manufacturer. Since the guides 28 have been designed to substantially not move and/or move only within certain minimal parameters, an expelling tampon 40, once it meets the guides 28, will optimally be caused to expel directionally from the tampon holder tube 22 by the angular surfacing of the guidance plates 29.

Each guidance plate 29 preferably comprises guidance ridges 30 (FIGS. 2–2A), continuous surfaces 32 (not shown) and at least two sloping surfaces 34 (not shown) for every guidance plate 29. For more detailed information on the structure of the guidance plates 29 herein, please see U.S. patent application Ser. No. 09/336,399, filed on Jun. 18, 1999 by Mackay, et al. and entitled Tampon Applicator, such patent application being hereby incorporated by reference herein. As mentioned before, each guidance plate 29 resides on the internal surface 28A of each guide 28. The guidance plate 29 is attached to and preferably juts out from its respective internal surface 28A (not shown). Herein, the angular surfaces that directionally expel a tampon 40 are preferably provided by the combined structure of the guidance ridges 30, continuous surfaces 32 and sloping surfaces 34 being fitted and working together. While not wishing to be bound by any particular theory, it is believed herein that the combination created in a guidance plate 29 (i.e., the guidance ridges 30, continuous surface 32, and sloping surfaces 34) helps to provide angled expulsion (i.e., directional expulsion) of a tampon 40 in conjunction with the guides 28. Directional expulsion of a tampon 40 is an important requirement and objective of any tampon applicator embodiment discussed herein.

For each of the embodiments noted above, the guidance plates 29 therein may be inwardly oriented towards the hollow of the tampon holder tube at an angle β ranging from about 0° to about 89° (FIG. 2A). Preferably, each guidance plate herein is inwardly oriented towards the hollow of the tampon holder tube at an angle β ranging from about 10° to about 80°. More preferably, each guidance plate is inwardly oriented towards the hollow of the tampon holder tube at an angle β ranging from about 20° to about 70°. The angle D is measured between the x-axis and y-axis shown. These same axes exist for the right oriented guidance plate 29 on the right oriented guide 28. The guidance plate 29 shown in FIG. 2A is the left oriented guidance plate 29; however, the right oriented guidance plate 29 will preferably tilt toward the x-axis at the same angle β as the left oriented guidance plate 29. In an alternative embodiment herein it is conceived that the left and right oriented guidance plates 29 may tilt toward their common x-axis at differing angles.

With regard to the orientation and structure of the guides 28, in one embodiment herein, the external surface 28B of each of the guides 28 is continuous or substantially continuous (FIGS. 1–3). By the term "continuous" it is meant herein that the external surface of the guides are substantially without any indentations, wedges, holes, or impressions. The internal surface 28A of this same guide 28 comprises at least one guidance ridge 30. As is seen in FIG. 2, a guidance ridge 30 may be a line or an area positioned toward the hollow portion 26' of the tampon applicator 20. As has been previously noted, the guidance ridge 30 may be created by one or more indentations in a guide 28 or additionally by one or more solid structures (not shown) formed onto the inner surface 28A of the guide 28. While not wishing to be bound to any particular theory, it is believed that where a solid structure exists attached to the internal surface 28A of a guide, it reinforces the guidance plate 29 and also helps to provide directional expulsion of a tampon 40 at its expulsion from a tampon holder tube 22.

FIG. 10 provides a view of an alternative embodiment to that shown in FIGS. 1–4. Specifically, the embodiment of FIG. 10 provides, in one case, only guidance ridges 30 raised from the internal surface 28A of each guide 28, and in another case, a combination of guidance ridges 30 and sloping surfaces 34 (not shown), i.e., generally, one sloping surface 34 per guidance ridge 30. Obviously, a continuous surface between the guidance ridges 30 is not present in this embodiment. Herein, a guidance plate 29 is still considered to be present. It exists, however, without the presence of a continuous surface unlike the previous embodiment. FIG. 10A is a bottom view of the tampon holder tube 22 of FIG. 10. In FIG. 10A, the guidance ridges 30 are shown to extend from the throughout length of the internal surface 28A on the guides 28. It noted herein, though, that the length of the guidance ridges 30 may depend upon the type of tampon used (i.e., its configuration) and/or the type of directional expulsion sought by a manufacturer and thus may be shortened in length as is necessary.

The embodiment shown in FIG. 10 is important because it offers an alternative in the amount of materials used to create a guidance plate 29 and in the overall construction of the tampon applicator 20. By using only guidance ridges 30 and/or guidance ridges 30 in combination with sloping surfaces 34, material which would otherwise be used to provide the continuous surface 32 is negated, thus saving possible additional material costs. Also, performance is not generally sacrificed by providing guidance ridges 30 only or in combination with sloping surfaces 34 because the guidance ridges 30 by their stiffness and rigidity in combination with the stiffness of the guides 28 will still serve to adequately directionally expel a tampon 40 from the tampon holder tube 22. As in the previous embodiment, the sloping surfaces 34 rising from the internal surfaces 28A of the guides 28 serves to provide additional angularity in the expulsion of a tampon 40.

Figure 7:
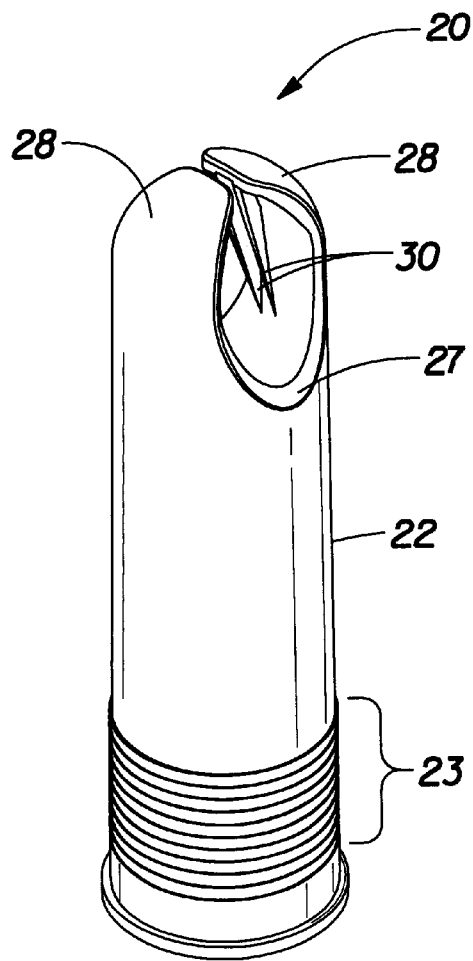
FIG. 7 is a perspective view of an alternative tampon applicator embodiment.
Figure 7A:
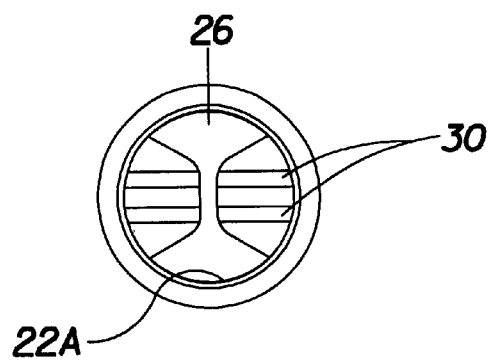
FIG. 7A is a bottom view of one embodiment of the tampon applicator of FIG. 7.
Figure 8:
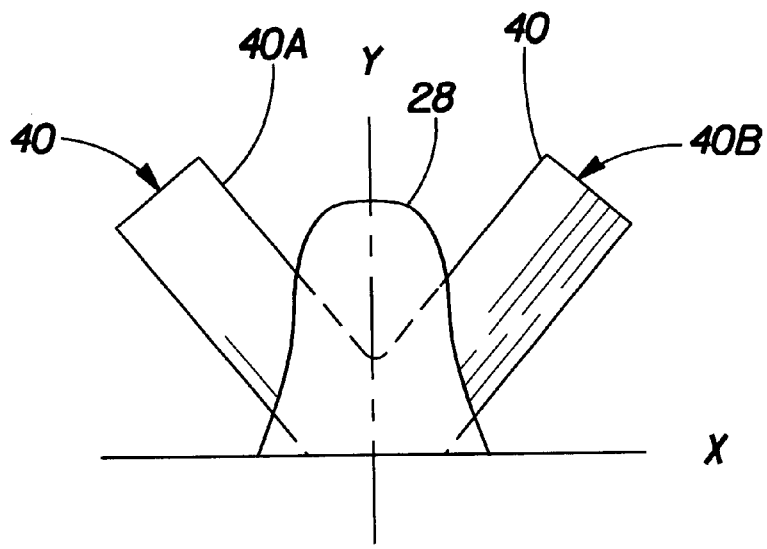
FIG. 8 is plan partial view of the expulsion end of the tampon applicator showing a tampon expelling therefrom.

In another embodiment herein, the external surface 28B of the guides 28 may be discontinuous (FIGS. 7–9). By the term "discontinuous" it is meant herein that the external surface of the guides 28 may comprise indentations, wedges, or impressions. In the embodiment shown in FIG. 7, the internal surface 28A of each guide 28 comprises at least one guidance ridge 30, and preferably a pair thereof As can be readily appreciated in FIGS. 7–9, the guidance ridges 30 in this embodiment will preferably, but not always, correspond directly to the indentations formed into the external surface 28B of each guide 28. Like the embodiment shown in FIGS. 10 an 10A, this embodiment constitutes a preferred embodiment because no additional material is being added to the tampon holder tube 22 to form a separate guidance plate 29. In fact, a guidance plate 29 is being impressed into each guide without sacrificing either performance in the guides themselves or the necessary rigidity in each guide 28. This embodiment would therefore be highly preferred in creating a low-cost tampon applicator.

In a highly preferred embodiment herein, the tampon holder tube 22 of the tampon applicator 20 comprises a pair of opposed guides 28 extending from the expulsion end and a pair of opposed free expulsion areas 26, the free expulsion areas 26 being positioned adjacent to the guides 28. (FIGS. 2, 4, 8A, 9 and 13). The "free expulsion area" it is meant herein to be an opening through which a portion of a tampon 40 may be directionally expelled. The free expulsion areas 26 and the guides 28 operate together to provide directed expulsion of the tampon 40 at expulsion through the tampon holder tube 22.

More specifically, when a tampon 40 is expelled through the tampon holder tube 22, and as it moves through the expulsion end 24 of the tampon holder tube 22, the tampon 40 is simultaneously (or substantially therefor) both directionally expelled by force against the guides 28 and resistance to opening provided by the guides 28 causing the directional shift or expulsion of the tampon 40 through the free expulsion areas 26, each free expulsion area 26 being positioned opposite to one-another on the holder tube 22 at the expulsion end 24 thereof In practice, the free expulsion areas 26 allow a substantially unobtrusive exit of the tampon 40 through the expulsion end 24 of the tampon holder tube 22. Furthermore, at expulsion, the tampon 40 is forced to at least partially divide or separate, thus providing at least two portions 40A, 40B of the tampon 40 which will preferably contact at least two surfaces of a female user's vaginal cavity.

The configuration of the free expulsion areas 26 are preferably created to match the configuration of the trajectory of the expelling tampon 40, such trajectory preferably being imposed by the angular configuration of the guides 28. In similar fashion, the guides 28 are created to provide a resistance to applied force to the tampon 40 as it is pushed through the tampon holder tube 22. Note that such pushing through or expulsion is normally conducted by a female user either digitally by use of one or more of her fingers or by a plunger 25 (FIG. 1). It is further noted herein that the shape or configuration of the free expulsion areas 26 may vary as long as full expulsion of the tampon 40 is allowed. One of skill in the art will readily recognize obvious variants on those presented in the patent application herein.

In FIGS. 2, 4, 8A and 9, the free expulsion areas 26 are shown as being oval or semi-oval in shape with a preferred beveled lip 27 turned inwardly towards the free expulsion area 26 of the holder tube 22. One versed in the art can imagine that the free expulsion areas 26 might be more circular, square, rectangular, triangular or any other conceivable shape possible as long as any such shape would work effectively to fully and properly expel a tampon 40 from the tampon holder tube 22. The free expulsion areas 26 are in no way limited by the size or shape that they may assume except that they should not hinder directional expulsion of a tampon 40.

While not wishing to be bound by any particular theory, it is believed herein that several unique elements work together to provide directional expulsion of a tampon 40 for side-to-side coverage. They include, but not exclusively so, the stiffness and interior surfaces of the guides 28, the guidance plates and the presence and shape of the expulsion areas 26. It is noted herein that directional expulsion of a tampon 40 may occur with only the guides 28 present, but for the preferred efficiency in directional expulsion, at least one other element should be included with the guides 28.

With regard to the stiffness of the guides 28, it is preferred to provide guidance ridges stiff enough to substantially resist moving as the un-joined and/or semi-joined portions of a tampon 40 expel therethrough (See FIGS. 12A–12B). However, such guidance ridges must also open at least slightly, thus becoming wide enough for the base of a tampon to move through the guidance ridges without substantial obstruction thereof In practice, the guides 28, because of their stiffness and/or resistance to move substantially out of place, substantially cause the directional expulsion of the tampon 40 as it moves through and out of the tampon holder tube 22, such directional expulsion being a critical feature of obtaining side-to-side coverage of the tampon 40 to a female user's vaginal cavity. As the tampon 40 moves through the tampon holder tube 22 and out through the expulsion end 24 of the tampon holder tube 22, the tampon 40 (i.e., the un-joined sections 40A, 40B and the semi-joined sections 40C, 40D thereof) is caused to substantially directionally divide. (FIGS. 10, 11 A, and 11B). As the tampon 40 exits the tampon applicator 20 and is positioned within a female user's vaginal cavity, the split portions 40A, 40B (FIG. 11A) or 40C, 40D (FIG. 11B) of the tampon 40 will preferably contact the sides and/or walls of a female user's vaginal cavity, thus enabling side-to-side coverage. Herein, the un-joined and/or semi-joined portions of a tampon will preferably divide from between about 5 mm to about 60 mm depending upon the design of the tampon applicator 20 when inserted into the vaginal cavity of a female user; e.g., see the length (L) in FIGS. 14A and 14B. Such length (L) of division of the tampon's un-joined sections (40A and 40B) or semi-joined sections (40C and 40D) is at the discretion of a manufacturer, but depends on the range of lateral width of a female user's vaginal cavities.

In a particularly preferred embodiment of the present invention, the guides 28 at least partially separate the tampon 40 into at least two distinct portions 40A and 40B as the tampon 40 is expelled from the tampon holder tube 22. Alternatively, the guides 28 substantially separate the tampon 40 into at least two distinct portions 40A and 40B as the tampon 40 is expelled from the tampon holder tube 22. Also alternatively, the guides 28 may merely indent and not separate the tampon 40 as it is expelled from the tampon holder tube 22.

The tampon holder tube 22 is preferably an elongate hollow tube that has insertion end (or "expulsion end") 24 and a gripping end 23. The tampon holder tube 22 can be constructed from similar materials to other tampon holder tubes known in the art of the type used in tampon applicators currently in use. Examples of other such tampon holder tube are described in U.S. Pat. No. 5,346,468 issued to Campion, et al. on Sep. 13, 1994, and U.S. Pat. No. 5,558,631 issued to Campion, et al. on Sep. 24, 1996. The tampon holder tube 22 can be of any suitable cross-sectional shape. Suitable cross-sectional shapes include, but are not limited to circular, oval, flattened circular, and elliptical. Preferably, the tampon holder tube 22 has a circular cross-sectional configuration.

The plunger 25 comprises a component that is used to expel a tampon 40 from its position within the tampon holder tube 22 when the plunger 25 is pushed manually into the tampon holder tube 25. The plunger 25 can be any type of component that is suitable for this purpose. The plunger 25 can be constructed similarly to plungers of the type used in tampon applicators currently in use. An example of a suitable plunger is described in U.S. Pat. No. 5,346,468 issued to Campion, et al. on September 13, 1994, and U.S. Pat. No. 5,558,631 issued to It should also be understood that the plunger 25 is an optional, but preferred component for use with the tampon applicator 20, and that the tampon applicator 20 will be fully functional if the plunger 25 is omitted, i.e., a user must insert and push the tampon 40 through the tampon applicator 20 digitally.

To use the tampon applicator 40 of the present invention the user will typically hold the tampon holder tube 22 in one hand at the finger grips on the same. When present, the user holds the end of the plunger 25, such as with her thumb and middle finger, and pushes the plunger 25 inwardly to slide the plunger 25 within the tampon holder tube 22. In practice, a user pushes the inserted plunger 25 until the entire tampon 40 is deployed from the tampon applicator 20. The user then pulls the entire tampon applicator 20 (i.e., with the plunger 25 inside) out of the user's vaginal opening.

As is seen in FIG. 15, the PRIOR ART device is a typical device in which the guides or petals thereof move readily away from the tampon as it is expelled from the tampon holder tube. Obviously, from such a construction, the tampon applicator of FIG. 15 can provide little if any directional expulsion of a tampon within the vagina of a female user and thus can provide no side-to-side coverage of a tampon within the vagina of a female user. All of the embodiments provided herein, except the PRIOR ART device, are designed to provide directional expulsion of a tampon which is critical to achieving side-to-side coverage of a tampon within a female user's vagina.

EXAMPLES

Example No. 1
"V" 14 mm Tubular—(2Tubes side by side w/punch & loop cord attachment and PP Overwrap width)

| Materials Needed: | Supplier: |
| --- | --- |
| 1. Overwrap. | 1. Sandler |
| 2. Absorbent Core. | 2. Procter & Gamble |
| 3. Cord. | 3. Wehadkee |
| 4. Thread. | 4. Coats America Thread |

PRODUCTION AIDS NEEDED:

| Sewing Machine | 25.4 × 160 mm Core Die Cutter |
| --- | --- |
| Embroidery Needles | Plastic formed into a Funnel |
| Darner Needles | Ezy-Pull Bodkin (Inverting tool) |

TAMPON MAKING INSTRUCTIONS ("V"14 mm PP Overwrap)

Using the 25.4×160 mm Die "Core" Cutter, cut the strips of Tampax Regular absorbency core material and set aside. Cut a (minimum of 150 mm) long section of Sandler polypropylene overwrap and place onto the work surface. Fold the PP overwrap in half lengthwise. Align the PP folded edge with the 14 mm marking on the sewing machine and sew a seam along the length of the PP forming a tube. Trim any excess materials from the sewn edge to ensure smooth edges. Using the Ezy-Pull tool, invert the PP tubing. (Ensuring that sewn seam is inside of the tube). Place the core material on the plastic, fold it in half and roll to form a funnel out of the plastic and a tube out of the core material. Insert the materials into the pre-made PP tubing (pulling core through and removing plastic tube). Try to ensure that the folded edge of the core with the seam line of the tubing run together if at all possible.

Cut the tubes to 60 mm in length. Align 260 mm tubes side by side (seam to seam). Using a Darning Needle push through outside of $1_{st}$ tube into the center of the second tube and out the side. Pull additional string throughout the two tubes. Bring the strings together and loop around. Trim the cord to 120 mm and the tampon tubes to 60 mm for a total tampon/string length of 180. Trim the ends to ensure they are smooth and neat.

Example No. 2
"V"14 mm Tubular—(PP Overwrap width)

| Materials Needed: | Supplier: |
| --- | --- |
| 1. Overwrap. | 1. Sandler |
| 2. Absorbent Core. | 2. Procter & Gamble |
| 3. Cord. | 3. Wehadkee |
| 4. Thread. | 4. Coats America Thread |

PRODUCTION AIDS NEEDED:

| Sewing Machine | 25.4 × 160 mm Core Die Cutter |
| --- | --- |
| Embroidery Needles | Plastic formed into a Funnel |
| Darner Needles | Ezy-Pull Bodkin (Inverting tool) |

TAMPON MAKING INSTRUCTIONS ("V"14 mm PP Overwrap)

Using the 25.4×160 mm Die "Core" Cutter, cut the strips of Tampax Regular absorbency core material and set aside. Cut a (minimum of 150 mm) long section of Sandler polypropylene overwrap and place onto the work surface. Fold the PP overwrap in half lengthwise. Align the PP folded edge with the 14 mm marking on the sewing machine and sew a seam along the length of the PP forming a tube. Trim any excess materials from the sewn edge to ensure smooth edges. Using the Ezy-Pull tool, invert the PP tubing. (Ensuring that sewn seam is inside of the tube). Place the core material on the plastic, fold it in half and roll to form a funnel out of the plastic and a tube out of the core material. Insert the materials into the pre-made PP tubing (pulling core through and removing plastic tube). Try to ensure that the folded edge of the core with the seam line of the tubing run together if at all possible.

Fold the tube of core material/overwrap in ½, ensuring that the inverted seam of the tube will be in the center (i.e., inside) of the "V", and then flatten by hand. From the fold measure up 60 mm to the tag ends (open ends) of the tube of core material/overwrap and trim the tag ends to ensure the ends are smooth and neat and the product measures 60 mm.

Remove a 180 mm section of cord. Tie a double overhand knot in one end of the cord. Trim the cord to measure 120 mm. Using a large darning needle pass the cord through the folded/seam side of the "V".

Example No. 3
SEWN "V" & KITE

| Materials Needed: | Supplier: |
|---|---|
| 1. Overwrap. | 1. Sandler |
| 2. Absorbent Core. | 2. Procter & Gamble |
| 3. Cord. | 3. Wehadkee |
| 4. Thread. | 4. Coats America Thread |
| 5. Absorbent core tube. | 5. A. Fem. |

PRODUCTON AIDS NEEDED:
  Sewing Machine
  Sewing Needles
  Crochet Hook
  "V" Template

TAMPON MAKING INSTRUCTIONS

Cut a 180 mm section of absorbent core tube, trim/remove the large section of this cord, trimming to sewn seam and set aside. Cut a 400 mm section of Tampax Regular core material, divide this section of Core Material into 2, ½ thickness. Again divide these ½ thick sections in half giving a total of 4, ¼ thick sections. Cut 4 200 mm sections of overwrap material, place one of these sections flat onto the surface of a table. Place one of the ¼ thickness of Core Material onto the sheet of Overwrap lengthwise, fold the overwrap over the Core Material sandwiching the Core Material between the overwrap. Repeat this process and you should have 2, ¼' cores sandwiched between the overwrap.

Using a sewing machine, sew along the long open edge (approximately ½ inch from edge) the entire length (making sure to sew through the edge of the Core Material) of the above piece. Trim off excess edge material and repeat for the other half.

Cut these sections into 80 mm sections. Take these 2 sections and place them on top of each other, align the edges and place the template onto these materials, aligning the top of the template along the sewn edge. Using a sewing machine sew along the edge of the template (note: do not sew along the edge that is already sewn). Trim off excess material making a V/Kite and place aside.

Take the trimmed section of the absorbent core tube and tightly attach a 200 mm section of Cord to the center of the absorbent core tube using two overhand knots. Pass the large end of the crochet hook through the open end of the V/Kite out the bottom point of the V/Kite, hook the cord and pull it through the V/Kite core sandwiches, sliding the section of the absorbent core tube into the V/Kite. Pull the absorbent core tube tightly into the V/Kite and using the crochet hook tightly place the absorbent core tube to the sides of the V/Kite. Using the sewing machine sew through the V/Kite along the edge of the absorbent core tube securing the absorbent core tube in place. Trim off excess absorbent core tube at top and trim cord to 130 mm from base of V/Kite.

If you are specifically making a "V" (i.e., not a Kite) to finish the prototype, you need to cut the center pocket out of the Kite, therefore, leaving a "V".

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

What is claimed is:

1. A tampon and tampon applicator in combination for directional expulsion of the tampon into the vaginal cavity of a female user, comprising:
   a tampon holder tube having a hollow portion, interior and exterior surfaces, a longitudinal axis, an expulsion end dimensioned for insertion into body cavity, and an insertion end positioned oppositely to the expulsion end, the tampon holder tube comprising a pair of guides oppositely faced and positioned across from one-another, each said guide having an external surface facing away from the hollow portion of the tampon holder tube and an internal surface facing inwardly toward the hollow portion of the tampon holder tube, the guides being positioned at the expulsion end of the tampon holder tube;
   a tampon loaded into the tampon holder tube in a pre-expelled position; and
   a plunger telescopically and slidably mounted in the tampon holder tube at the insertion end of the tampon holder tube, the plunger being adapted to expel the tampon thought the tampon holder tube and out from the the pair of guides to effect the directional expulsion of the tampon from the tampon holder tube.

2. The tampon and tampon applicator of claim 1 wherein the feature for directional expulsion partially separates at least one portion of the tampon into at least two distinct portions as the tampon is directionally expelled from the tampon holder tube.

3. The tampon and tampon applicator of claim 2 wherein the feature for directional expulsion substantially separates at least one portion of the tampon into at least two distinct portions as the tampon is expelled from the tampon holder tube.

4. The tampon and tampon applicator of claim 1 wherein the external surfaces of the guides are continuous.

5. The tampon and tampon applicator of claim 1 wherein the external surfaces for the guides are discontinuous.

6. The tampon and tampon applicator of claim 5 wherein the discontinuous external surfaces of the guides are indented inwardly toward the hollow portion of the tampon holder tube such that the discontinuous external surface forms indentations in the discontinuous external surface.

7. The tampon and tampon applicator of claim 6 wherein the indentations of the guides forms each said guidance plate on the internal surface of each said guide.

8. The tampon and tampon applicator of claim 1 wherein the guides each have a pre-expelled position prior to expulsion of the tampon through the tampon holder tube.

9. The tampon and tampon applicator of claim 8 wherein each said guide comprises at least one guidance plate positioned onto the internal surface of the guide, each said guidance plate being oriented to face inwardly toward the hollow portion of the tampon holder tube.

10. The tampon and tampon applicator of claim 9 wherein each said guidance plate comprises at least one pair of spatially opposed guidance ridges, each said guidance ridge being spaced apart and having a continuous surface positioned therebetween the pair of the guidance ridges.

11. The tampon and tampon applicator of claim 9 wherein the guidance plate further comprises a pair of sloping surfaces, each said sloping surface being held adjacent to and sloping downwardly from one said guidance ridge to the internal surface of the guide.

12. The tampon and tampon applicator of claim 9 wherein each said guidance plate is inwardly oriented towards the hollow portion of the tampon holder tube at an angle $\beta$ ranging from about 0° to about 89°.

13. The tampon and tampon applicator of claim 9 wherein each said guidance plate is inwardly oriented towards the hollow portion of the tampon holder tube at an angle β ranging from about 10° to about 80°.

14. The tampon and tampon applicator of claim 9 wherein each said guidance plate is inwardly oriented towards the hollow portion of the tampon holder tube at an angle β ranging from about 20° to about 70°.

15. A tampon and tampon applicator in combination for directional expulsion of the tampon into the vaginal cavity of a female user, comprising:

a tampon holder tube having a hollow, interior and exterior surfaces, a longitudinal axis, and an expulsion end dimensioned for insertion into a female's vaginal cavity, a tampon loaded into the tampon holder tube in a pre-expelled position, the tampon holder tube comprising a feature for directionally expelling the tampon, the feature comprising a pair of opposed guides extending from the expulsion end, each said guide having a continuous external surface and an internal surface opposed thereto, wherein the continuous external surface faces away from the hollow of the tampon holder tube and the opposing internal surface faces inwardly toward the hollow of the tampon holder tube, the internal surfaces each having a guidance plate positioned inwardly toward the hollow of the tampon holder tube, each said guidance plate further comprising at least one pair of guidance ridges with a continuous surface positioned therebetween and a pair of sloping surfaces, each said sloping surface being positioned adjacent to a guidance ridge and sloping from the guidance ridge to the internal surface of the guide, the tampon holder tube further comprising a pair of free expulsion areas positioned adjacent to the guides on the tampon holder tube, the free expulsion areas and the guides operating together to provide directional expulsion of a tampon.

16. A tampon and tampon applicator in combination for directional expulsion of the tampon into the vaginal cavity of a female user, comprising:

a tampon holder tube having a hollow, interior and exterior surfaces, a longitudinal axis, and an expulsion end dimensioned for insertion into the female's vaginal cavity, a tampon loaded into the tampon holder tube in a pre-expelled position, the tampon holder tube comprising a feature for directionally expelling the tampon, the feature comprising a pair of opposed guides extending from the expulsion end, each said guide having a discontinuous external surface and an internal surface opposed thereto, wherein the discontinuous external surface faces away from the hollow of the tampon holder tube and the opposing internal surface faces inwardly toward the hollow of the tampon holder tube, the discontinuous external surfaces each being indented inwardly toward the hollow of the tampon applicator, each said indentation operating to form a guidance plate on the internal surface of each said guide, the feature further comprising a pair of opposed free expulsion areas, the free expulsion areas being positioned adjacent to the guides on the tampon holder tube, the free expulsion areas and the guides operating together to provide directed expulsion of a tampon.

17. A tampon and tampon applicator in combination for directional expulsion of the tampon into the vaginal cavity of a female user, comprising:

a tampon holder tube having a hollow, interior and exterior surfaces, a longitudinal axis, and an expulsion end dimensioned for insertion into a female's vaginal cavity, a tampon loaded into the tampon holder tube in a pre-expelled position, the tampon holder tube comprising a feature for directionally expelling the tampon, the feature comprising a pair of opposed guides extending from the expulsion end, each said guide having an external surface and an internal surface opposed thereto, wherein the external surface faces away from the hollow of the tampon holder tube and the opposing internal surface faces inwardly toward the hollow of the tampon holder tube, the internal surfaces each comprising at least one pair of guidance ridges, each said guidance ridge substantially extending throughout the expulsion end of the tampon applicator, the feature further comprising a pair of opposed free expulsion areas, the free expulsion areas being positioned adjacent to the guidance ridges on the tampon holder tube, the free expulsion areas and the guides operating together to provide directed expulsion of a tampon.

* * * * *